United States Patent [19]

Waltke

[11] 4,288,220
[45] Sep. 8, 1981

[54] DENTAL CASTS HAVING VERTICAL ADJUSTMENTS

[75] Inventor: Robert W. Waltke, Bayside, N.Y.

[73] Assignee: Pennwalt Corporation, Philadelphia, Pa.

[21] Appl. No.: 135,805

[22] Filed: Mar. 31, 1980

[51] Int. Cl.³ .............................................. A61C 19/00
[52] U.S. Cl. .................................................... 433/74
[58] Field of Search ............................. 433/74, 36, 176

[56] References Cited

U.S. PATENT DOCUMENTS

| | | | |
|---|---|---|---|
| 1,780,117 | 10/1930 | Craigo | 433/74 |
| 3,153,283 | 10/1964 | Weissman | 433/176 |
| 3,470,614 | 10/1969 | Kelly | 433/36 |
| 3,798,772 | 3/1974 | Eberhard | 433/74 |
| 4,021,916 | 5/1977 | Spalten | 433/74 |
| 4,056,585 | 11/1977 | Waltke | 433/74 |

FOREIGN PATENT DOCUMENTS 2515445  10/1976  Fed. Rep. of Germany ........ 433/74

*Primary Examiner*—Gene Mancene
*Assistant Examiner*—John J. Wilson

[57] ABSTRACT

A stanchion assembly is adjustably supported in spaced relationship over an edentulous area of a negative dental impression. A dental cast formed from the impression includes an edentulous portion replicating the edentulous area. The edentulous portion is made detachable from the cast and has a thickness determined by said space provided. The assembly includes a parting plate removable from the cast. By replacing the removed plate with a spacer of greater or lesser thickness, the edentulous portion will be raised or lowered respectively precisely by an amount equal to the difference in thickness of the parting plate and its replacement spacer.

10 Claims, 6 Drawing Figures

DENTAL CASTS HAVING VERTICAL ADJUSTMENTS

STATEMENT OF THE INVENTION

This invention relates to apparatus for making models of teeth wherein an edentulous portion thereof is detachable therefrom and vertically adjustable therein.

BACKGROUND AND SUMMARY OF THE INVENTION

In that aspect of dentistry which relates to tooth restoration, it is often required that an accurate dental model be made in a dental stone material of the affected tooth or teeth and surrounding tissue areas. Many and various methods are known in the industry for providing such a model. For example, the split cast method involves making the model in two layers which are separable. Dowel pins are permanently fixed in one of the layers. If it becomes necessary to divide that layer into several sections, each section may readily be returned to its exact relative position by means of the dowels mating their respective holes in the integral layer. In such a system, the tooth dies and edentulous portions of the model may be removed and later inserted.

Several other methods produce a multi-layered model from a single casting procedure by placing a physical barrier into the negative impression prior to the casting of stone thereinto.

For example, in U.S. Pat. No. 3,470,614, a somewhat complicated pin and parting plate assembly is employed. In U.S. Pat. No. 3,153,283, a precise fit between a pin and sleeve is required.

In the above patents, and others, the parting plate, through the use of retentive media associated therewith, such as projections, grooves, and the like, render the parting plate an inseparable part of the final model.

The present invention discloses a dental model wherein edentulous portions thereof are detachable therefrom and vertically adjustable therein. The parting plate is discardable and may be replaced with a spacer of any desired thickness. The height of the edentulous portion of the dental model may therefore be raised, or lowered, with respect to the remainder of the teeth in the model, and precisely by the amount of difference between the thickness of the parting plate and selected spacer.

While an edentulous portion constructed to render it detachable from a model may be raised by the simple expediency of placing a shim thereunder, no present dental model making system is believed to teach methods or apparatus for its lowering. Advantages to be gained from edentulous portions capable of being lowered are several.

For example, pontic units on a fixed bridge should contact the tissues of edentulous areas to exert a very slight pressure thereupon in order to prevent food from being forced thereunder during mastication. Conversely, if the pontics exert excessive pressure, tissues become inflamed and unhealthy. Traditionally, dental casts were mechanically scraped or abraded in the edentulous portions in order that the pontics constructed thereupon would displace tissue proportionally to the amount abraded or removed from the dental cast or model.

Additionally, edentulous or ridge areas of a mouth are characterized by a complicated physiography comprising a series of depressions and raised areas which provide compound contiguous convexities and concavities. No method of uniformly scraping, abrading or removing such material is believed known or available. Consequently, many pontic units fit poorly. Further, many of these poorly fitting pontic units were made despite repeated visits to the dentist. An edentulous portion of a dental cast, which can be vertically adjusted, i.e., readily lowered as well as raised, obviates the need to meticulously scrape or abrade, which, as aforedescribed, often yet resulted in ill-fitting pontics.

Further, edentulous areas of recent origin are generally quite different from edentulous areas resulting from extractions of past years. More specifically, more tissue will be found over supporting bone substrate of recently formed edentulous areas. Thus, amount of tissue displacement presents another problem.

The present invention allows the dentist to prescribe an exact amount of tissue displacement for a given edentulous area which permits the technician to make more acceptable units.

To clarify more fully, most current fixed bridgework is of a type known as porcelain fused to metal. Porcelain powder is mixed with water to produce a paste-like slurry which forms the artificial teeth of a dental cast. When the shaping process is completed, the bridgework is removed from the model for firing in a kiln. During the firing process, the porcelain powder becomes a vitreous mass having a volume approximately 15% less than the original pre-fired mass. As a result of this shrinkage, a space develops under the pontic units of the bridge. In order to compensate, traditionally, a mass of porcelain slurry is added to the pontic units after the bridge has been removed therefrom but prior to its firing. The pontic will thus be oversized after firing requiring tedious grinding thereof in an attempt to mate the very complex surfaces of the edentulous portions of the dental cast.

In order to compensate for the porcelain shrinkage factor, the present invention, with its ability to provide for a lowering of the edentulous portion of the cast, additional porcelain may be built at the underside of the pontic. Thus, when the cast is brought back to its original configuration, only a minimal amount of adjustment by grinding will be necessary in order to insure a proper fit.

DETAILED DESCRIPTION OF THE INVENTION

Figure 1:
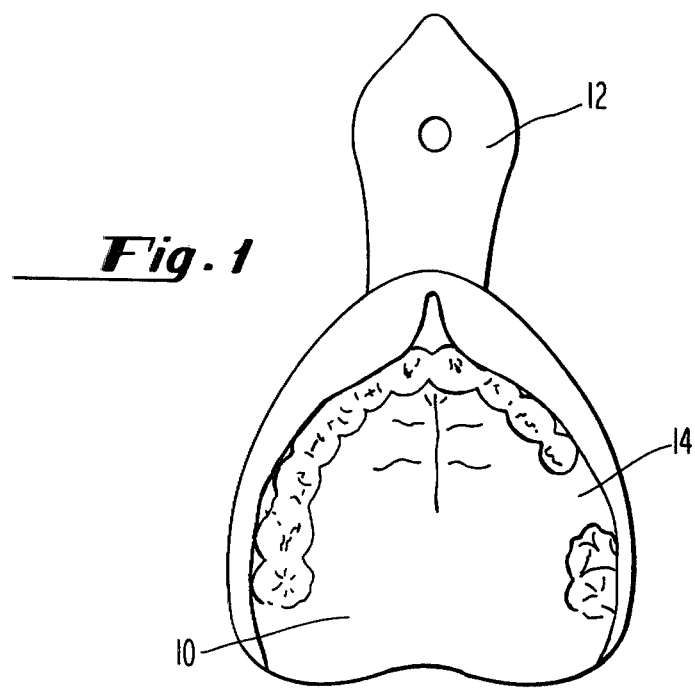
FIG. 1 is a plan view of a dental negative impression (with trays) which includes an edentulous area.

In FIG. 1, a wax or rubber negative or elastic mould or impression 10 of the patient's teeth and gums supports the stanchion assembly of the present invention, each being supported on a dental tray 12.

It is common practice, when making a model of a patient's teeth, to first form a negative impression thereof. The negative impression is filled with a die material to form a positive replica of the teeth. After the die material has cured or set, the model is completed by casting a base stone formed integrally with the die material to form a foundation for the replica of the teeth. An edentulous portion which is to be worked on is made removable from the model by cutting the die material by suitable means and separating the edentulous portion therefrom.

Figure 2:
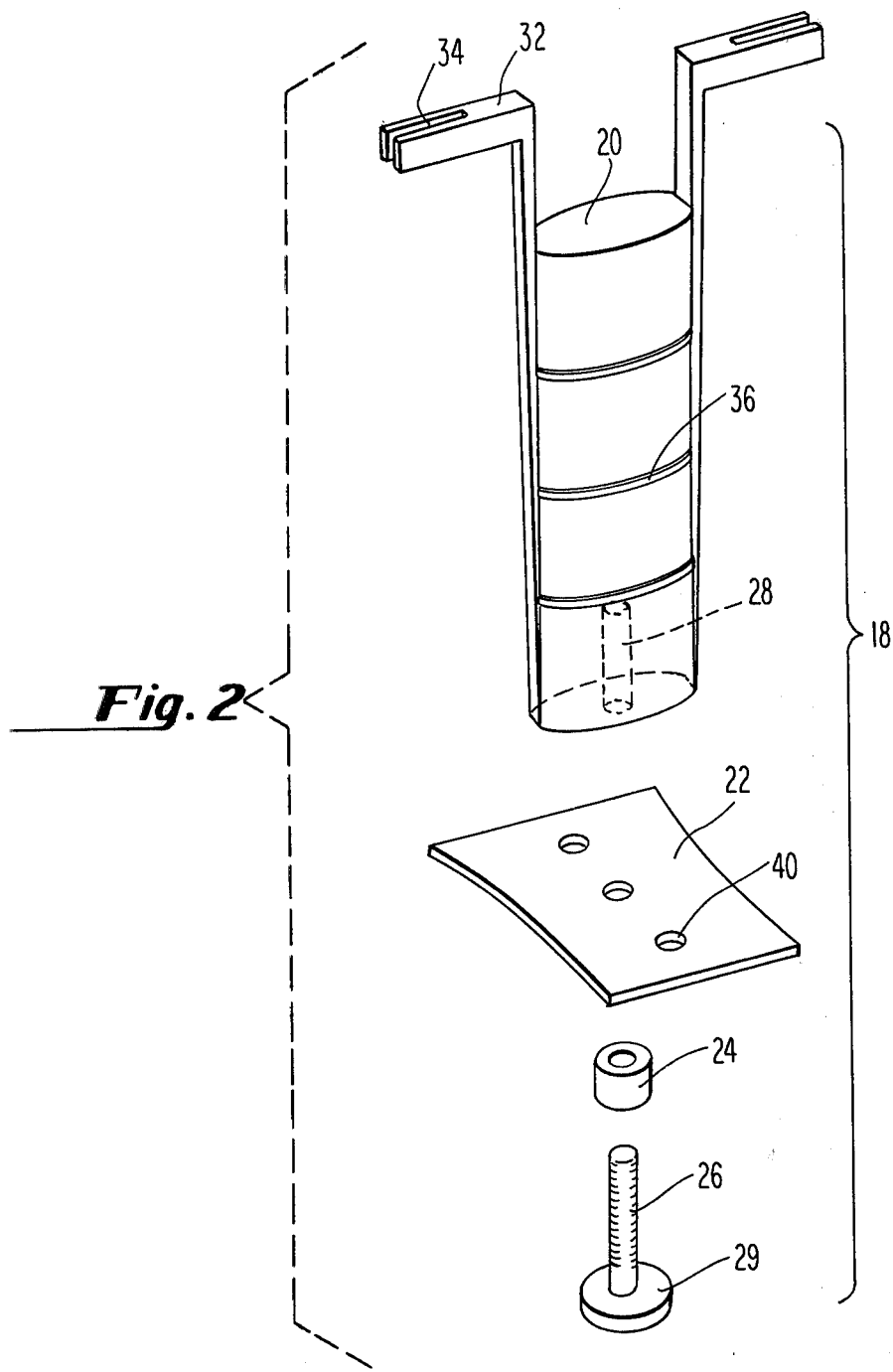
FIG. 2 is an exploded perspective view of a stanchion assembly used with the impression of FIG. 1 in making the detachable edentulous portion.

In preparing impression 10 for casting a detachable edentulous portion which replicates an edentulous area 14, a pair of straight pins 16 (FIG. 3) is inserted substantially vertically in the impression 10 on the buccolingual midline of the edentulous area 14. A stanchion assembly 18 (FIGS. 2 and 3) comprises a stanchion 20, parting plate 22, spacer 24, all releasably interconnected by means of a rivet 26 passing therethrough and received by an axial bore 28 at a lower portion of stanchion 20.

Stanchion 20 is suitably injection moulded from a tough abrasion resistant plastic which is solvent-proof and capable of withstanding boiling water. The stanchion includes a pair of opposed laterally extending mounting tabs 32, each having a slot 34 disposed therein along a substantial portion of its length for engaging mounting pins 16. Mounting tabs 32, in effect, form an interrupted bar member. Spaced retention rings 36 are moulded about stanchion 20 to assist in its permanent retention within the model. The stanchion is permanently retained in the model base.

Stanchion 20 is solid and illustrated as substantially elliptical in cross-section although other cross-sections are satisfactory, even circular, so long as retention rings 36 are provided therearound.

Figure 4:
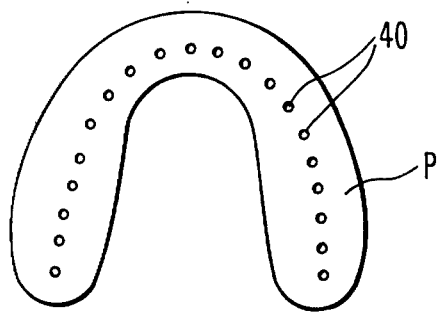
FIG. 4 is a plan view of a parting plate configured to resemble a typical dental arch.
Figure 5:
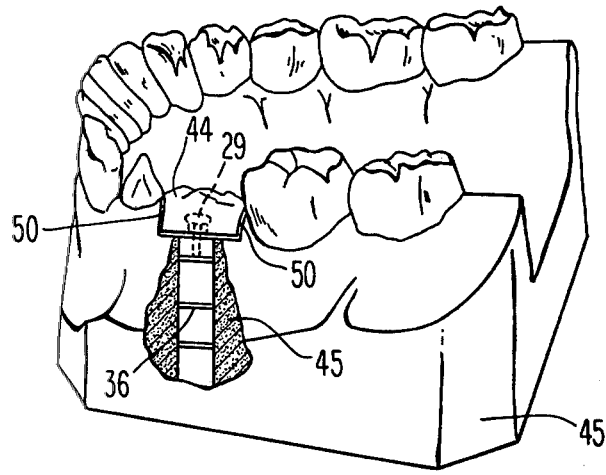
FIG. 5 is a perspective view, partially cutaway, of a dental cast illustrating rentention of stanchion of the stanchion assembly therewithin and locations of saw cuts made for detaching edentulous portion therebetween from the cast.
Figure 6:
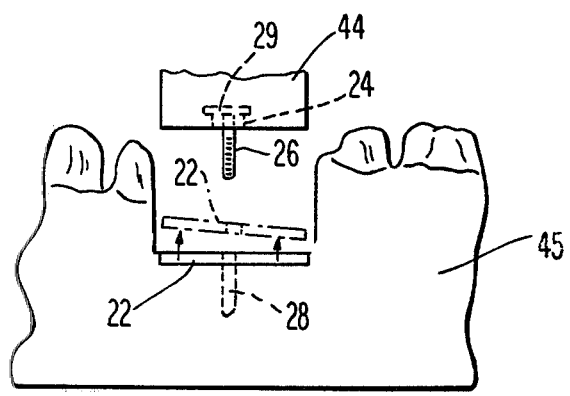
FIG. 6 is an elevational view illustrating detachability of the edentulous portion from the cast or model and discardability of parting plate therefrom.

Parting plate 22 is conveniently plastic, such as polypropylene, for example, and is cut from a suitable portion of a parting plate P (FIG. 4) formed to resemble a typical dental arch. After being cut from plate P, parting plate 22 may be trimmed. Plates P will be of various sizes and configurations to accommodate patients having varying sizes and shapes of dental arches. Parting plate P is provided with a plurality of spaced holes or orifices 40 through one of which, rivet 26 passes for frictional reception within bore 28 of stanchion 20. Rivet 26 is provided with a head 29 which helps to permanently anchor the rivet in detachable edentulous portion 44 (FIGS. 5 and 6). Spacer 24 is similarly permanently retained therein. Parting plate orifices 40, in addition to one of which serving as a passageway for rivet 26 into bore 28, permits bleeding of any entrapped air within the material being poured. It is appreciated that edentulous areas may embrace a plurality of adjoining missing teeth.

In making the dental cast or model 45 with a detachable edentulous portion 44, a pair of horizontal marks 48 are made (FIG. 3), conveniently with a ball point pen, one mark each along the buccal and lingual side of edentulous area 14. The marks will be transferred to stone model 45 for indicating the depth of proximal saw cuts 50 to be made when detaching edentulous portion 44 from cast or model 45, later described. Marks 48 are preferably made slightly longer than the length of parting plate 22 and are desirably approximately ½ cm above edentulous area 14.

Insert the two straight pins 16 into the impression 10, one bucally and the other lingually, centered on the buccolingual midline of edentulous area 14. The assembled stanchion assembly 18 is placed over edentulous area 14 such that parting plate 22 lightly contacts and rests upon both buccal and lingual edges of impression 10 as shown in FIG. 3 at the marks 48.

Final positioning of stanchion assembly 18 is effected through engagement of slots 34 with pins 16 which may be positioned vertically in negative mould 10 or angled as desired.

Figure 3:
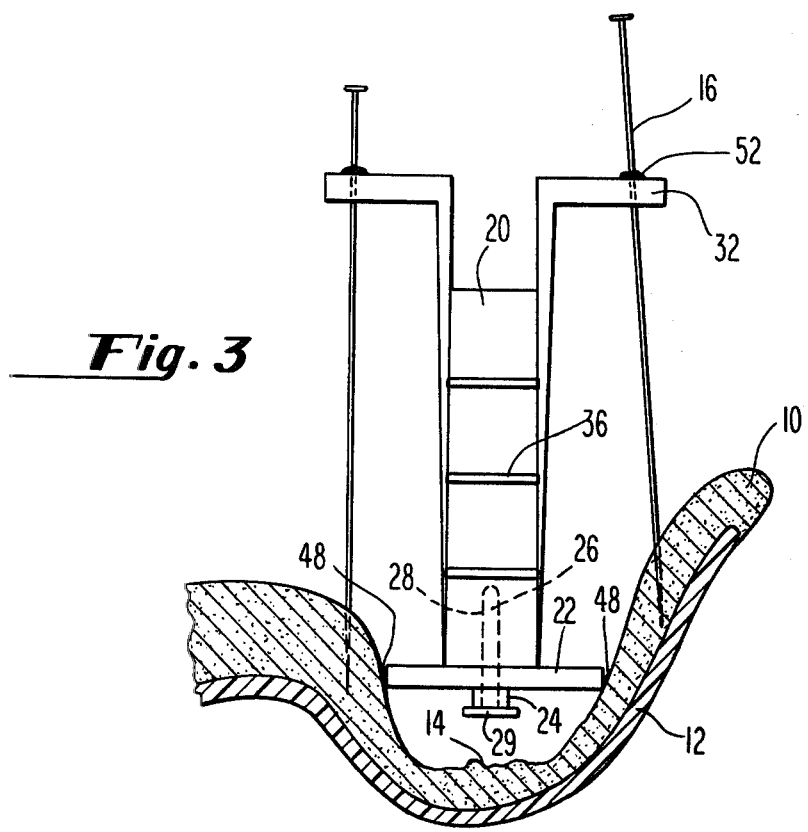
FIG. 3 is a partially sectioned view through the edentulous area illustrated in FIG. 1, including the stanchion assembly of FIG. 2 in operable position.

A hard resinous wax is flowed into the slots 34 of tabs 32 around pins 16 for sealing the contact therebetween, as indicated by the numeral 52 of FIG. 3.

The impression is now boxed with boxing wax, or alternatively, wrapped with a suitable masking tape. An aerosol liquid surface tension breaker may be applied at this point, if required. Upon drying of the surface tension breaker, if used, the model may be poured.

When the model is hard, separate it from the impression and extract pins. The model base may now be trimmed to size and shape and the mounting tabs snipped or ground off. A proximal saw cut 50 (FIG. 5) to a depth where marks 48 have been transferred to model 45 is made on each side of edentulous portion 44.

Edentulous portion 44 may now be detached from cast or model 45 by any suitable device or means.

As illustrated in FIG. 6, parting plate 22 is readily removable from model 45. By replacing parting plate 22 with a spacer of greater thickness, edentulous portion 44 will be raised by an amount equal to the difference between the thicknesses of the spacers. By replacing parting plate 22 with spacers of lesser thicknesses, it is now possible to lower the edentulous portion by specified amounts. Thus, in accordance with the present invention, edentulous portion 44 is vertically adjustable in either direction, i.e., it may be raised or lowered precisely by an amount equal to the difference in thickness between parting plate 22 and its replacement.

I claim:

1. Apparatus for preparing a dental cast from a negative dental impression, said cast having a detachable vertically adjustable edentulous portion replicating an edentulous area of said impression, said apparatus comprising pin means insertable in said impression adjacent said edentulous area, a stanchion assembly articulating with said pin means and positionable above said edentulous area in spaced relationship thereto, said stanchion assembly comprising a parting plate of substantially identical size and shape as said edentulous area, an upright stanchion positioned above said parting plate and having mounting means at its upper end for effecting said articulation with said pin means, holding means for releasably interconnecting said parting plate and stanchion, said holding means being permanently affixed to said edentulous portion, said parting plate being removable from said dental cast for substitution by another plate of different thickness whereby engagement therewith by said holding means and edentulous portion provides said vertical adjustability thereto, said vertical adjustability including raising and lowering of said edentulous portion depending upon difference in thickness between said parting plate and said another plate of different thickness.

2. The apparatus of claim 1 wherein said parting plate and stanchion are in contact relationship prior to said removal of said parting plate from said dental cast.

3. The apparatus of claim 2 wherein said parting plate is provided with at least one orifice therethrough, said stanchion is provided with an axial bore at its lower end, and said holding means includes a rivet comprising a head a stud attached to said head, at least a portion of said stud extending from said edentulous portion for passing through said orifice of said parting plate and into releasable engagement with said stanchion bore.

4. The apparatus of claim 3 wherein said holding means is further characterized by a spacer washer disposed between said rivet head and parting plate, said washer being of smaller diameter than diameter of said rivet head.

5. The apparatus of claim 3 wherein said stanchion is provided with retention rings therearound for permanently retaining said stanchion within said dental cast.

6. The apparatus of claim 3 wherein said pin means comprises a pair of straight pins.

7. The apparatus of claim 6 wherein said straight pins are inserted into said negative dental impression across buccolingual midline of said edentulous area.

8. The apparatus of claim 7 wherein said mounting means includes a pair of opposed laterally extending mounting tabs.

9. The apparatus of claim 8 wherein each of said mounting tabs is provided with a slot starting at its outer portion and running substantially the length of said tab, said slots being in alignment.

10. The apparatus of claim 9 wherein said parting plate is spaced approximately ½ cm above said edentulous area.

* * * * *